US006822136B1

(12) United States Patent
Niemeyer et al.

(10) Patent No.: US 6,822,136 B1
(45) Date of Patent: Nov. 23, 2004

(54) SWIMWEAR WITH BUILT-IN DRAINING MECHANISM

(75) Inventors: Michael John Niemeyer, Appleton, WI (US); Lawrence Howell Sawyer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 249 days.

(21) Appl. No.: 09/698,301

(22) Filed: Oct. 27, 2000

(51) Int. Cl.$^7$ ................................................ A61F 13/15
(52) U.S. Cl. ...................... 604/378; 604/364; 604/367; 604/375
(58) Field of Search ................................ 604/364, 365, 604/366, 367, 375, 386, 387, 389, 385.01, 393, 381, 383, 378

(56) References Cited

U.S. PATENT DOCUMENTS

| | | |
|---|---|---|
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |
| 3,542,615 A | 11/1970 | Dobo et al. |
| 3,613,686 A | 10/1971 | DeWoskin |
| 3,692,618 A | 9/1972 | Dorschner et al. |
| 3,802,817 A | 4/1974 | Matsuki et al. |
| 3,838,692 A | 10/1974 | Levesque |
| 3,849,241 A | 11/1974 | Butin et al. |
| 3,918,433 A | 11/1975 | Fuisz |
| 4,340,563 A | 7/1982 | Appel et al. |
| 4,555,245 A | 11/1985 | Armbruster |
| 4,663,220 A | 5/1987 | Wisneski et al. |
| 4,704,114 A | 11/1987 | Wilson et al. |
| 4,704,116 A | 11/1987 | Enloe |
| 4,940,464 A | 7/1990 | Van Gompel et al. |
| 5,046,272 A | 9/1991 | Vogt et al. |
| 5,085,654 A * | 2/1992 | Buell ........................ 604/370 |
| 5,104,116 A | 4/1992 | Pohjola |
| 5,224,405 A | 7/1993 | Pohjola |
| 5,226,992 A | 7/1993 | Morman |
| 5,236,428 A | 8/1993 | Zajaczkowski |
| 5,291,617 A | 3/1994 | Moretz et al. |
| 5,294,478 A | 3/1994 | Wanek et al. |
| 5,392,467 A | 2/1995 | Moretz et al. |
| 5,414,870 A | 5/1995 | Moretz et al. |
| 5,435,014 A | 7/1995 | Moretz et al. |
| 5,509,913 A * | 4/1996 | Yeo ............................. 604/34 |
| 5,509,915 A * | 4/1996 | Hanson et al. .............. 604/378 |
| 5,545,158 A * | 8/1996 | Jessup ...................... 604/385.3 |
| D377,980 S * | 2/1997 | Slingland ...................... D24/6 |
| 5,601,545 A | 2/1997 | Glaug et al. |
| 5,614,283 A | 3/1997 | Potnis et al. |
| 5,631,074 A * | 5/1997 | Herlihy, Jr. .................. 442/35 |
| 5,669,896 A | 9/1997 | Kielpikowski |
| 5,674,213 A | 10/1997 | Sauer |
| 5,792,132 A * | 8/1998 | Garcia ..................... 604/38.01 |
| 5,843,056 A * | 12/1998 | Good et al. ................. 604/367 |
| 5,876,394 A | 3/1999 | Rosch et al. |
| 6,009,558 A | 1/2000 | Rosch et al. |
| 6,049,916 A | 4/2000 | Rajala et al. |
| 6,610,901 B2 * | 8/2003 | McMahon-Ayerst et al. .... 604/378 |

FOREIGN PATENT DOCUMENTS

| | | |
|---|---|---|
| EP | 0 217 032 A2 | 4/1987 |
| EP | 0 677 284 A1 | 10/1995 |
| EP | 0 745 367 A2 | 5/1996 |
| EP | 0 750 894 A2 | 1/1997 |
| WO | WO 93/09740 | 5/1993 |
| WO | WO 98/44883 | 10/1998 |
| WO | WO 99/16400 | 4/1999 |

\* cited by examiner

*Primary Examiner*—John J. Calvert
*Assistant Examiner*—Jacqueline F. Stephens
(74) *Attorney, Agent, or Firm*—Pauley Petersen & Erickson

(57) ABSTRACT

An absorbent swimwear garment having a built-in draining mechanism for releasing excess swim water. The draining mechanism can include a liquid-permeable outer cover in a crotch area of the garment and/or liquid-permeable containment flaps. In addition, an absorbent assembly can be configured to direct incoming fluid away from the most liquid-permeable areas of the outer cover and containment flaps. During initial product use, the absorbent swimwear garment is able to contain urine and bowel movements, similar to ordinary diapers and training pants. When the swimwear garment is submersed in swim water, such as pool or lake water, the hydrostatic head of any excess water in the garment is sufficient to drain through the liquid-permeable outer cover and/or containment flaps, thereby allowing swim water, but not bowel movements, to drain out the bottom of the garment.

30 Claims, 4 Drawing Sheets

SWIMWEAR WITH BUILT-IN DRAINING MECHANISM

FIELD OF THE INVENTION

This invention is directed to disposable swimpants and swimsuits for pre-toilet trained children. More particularly, the swimwear has a built-in draining mechanism for draining swim water from the garment.

BACKGROUND OF THE INVENTION

Absorbent swim pants and swimsuits for pre-toilet trained children have absorbent cores and moisture barriers to prevent leaks of urine and bowel movements. Because the products are designed for leakage prevention, they retain sizable quantities of swim water, such as pool or lake water, during and after swimming. Some absorbent swim pants and swimsuits include containment flaps for additional leakage prevention. Containment flaps made of liquid impermeable material tend to retain even greater amounts of water within the garment than garments not having containment flaps. This retention of water is undesirable because it causes the pants to sag down, is uncomfortable for the wearer, can be uncontrollably released from the pant, and can soak towels and clothing after swimming.

There is a need or desire for an absorbent swimwear garment that provides uncompromised urine and bowel movement containment before swimming and allows the draining of excess water from the garment during and after swimming.

SUMMARY OF THE INVENTION

The present invention is directed to a pant-like absorbent swimwear garment, such as a swim pant or a swimsuit, that prevents pre-swim urine leakage while allowing large amounts of excess water to be drained from the garment after swimming. A built-in draining mechanism in the garment uses semi-permeable gasketing materials or barrier materials, thereby enabling the absorbent garment to absorb urine without retaining excessive amounts of swim water, such as lake or pool water, after the wearer leaves the lake or pool. More particularly, a portion or all of the gasketing or barrier system is permeable to swim water at least under hydrostatic head conditions that exist in the garment when the wearer exits the water.

In one embodiment of the invention, semi-permeable or permeable containment flaps are used around the leg openings of the garment. The material that is used to form the containment flaps can be permeable to aqueous fluids under all pressures or only under high hydrostatic pressure. The material can have a gradient of permeability, for example, being most permeable at the top of the flap to impermeable at the bottom. Permeability can be delivered by the base material structure or by secondary perforations. Alternatively, permeability can be induced through partial or selective dispersibility.

In another embodiment of the invention, a liquid permeable outer cover composite serves as the built-in drain mechanism. The permeability can be zoned into the lowest, most inconspicuous portion of the garment, the back crotch area. By locating a permeable zone in the bottom of the garment, the permeable portion can be designed such that it requires a higher hydrostatic pressure to induce fluid flow. By requiring higher hydrostatic pressure, small amounts of fluid having relatively low hydrostatic pressures, i.e., pre-swim urinary insults, are better contained within the garment. Permeability can be delivered by the base material structure or by secondary perforations. Alternatively, permeability can be induced through partial or selective dispersibility.

An absorbent assembly including superabsorbent materials, surge materials, stabilized airlaid absorbent structures, coformed material, fluff pulp, or combinations of any of these materials, or the like, can be included in the absorbent garment to maintain a low hydrostatic pressure against the permeable membrane prior to swimming. These absorbent materials can be configured different ways to achieve fast intake and void volume generation to prevent excess fluid from reaching the containment flaps or other barrier materials. These materials can also be configured to direct incoming fluid insults parallel to the longitudinal centerline of the pant and to inhibit fluid movement away from the longitudinal centerline toward the permeable flap materials. Urine can be retained in the capillary structure or by gelation.

Prior to swimming, the garment can contain urine and bowel movements like a typical diaper or training pant. When the garment is worn while swimming, the water may dilute any urine that may be present and aqueous fluids not held in the absorbent material may flow out the garment through the semi-permeable or permeable membrane of the garment. Bowel movement material is kept inside the garment because the liner material is constructed as in a normal absorbent garment, which allows fluids to pass through while keeping bowel movements and other solids contained.

The resulting product is an absorbent swimwear garment that provides uncompromised urine and bowel movement containment before swimming but allows the draining of excess water from the swim pant during and after swimming, thereby resulting in improved pant fit, thus greater comfort, during and after swimming. Improved fit can lead to better bowel movement containment while swimming. Furthermore, the fluid permeability of the gasketing membrane also results in improved garment breathability. Such fluid permeability enables the garment to dry quickly.

With the foregoing in mind, it is a feature and advantage of the invention to provide an absorbent swimwear garment with a built-in draining mechanism for draining excess swim water.

DEFINITIONS

Figure 1:
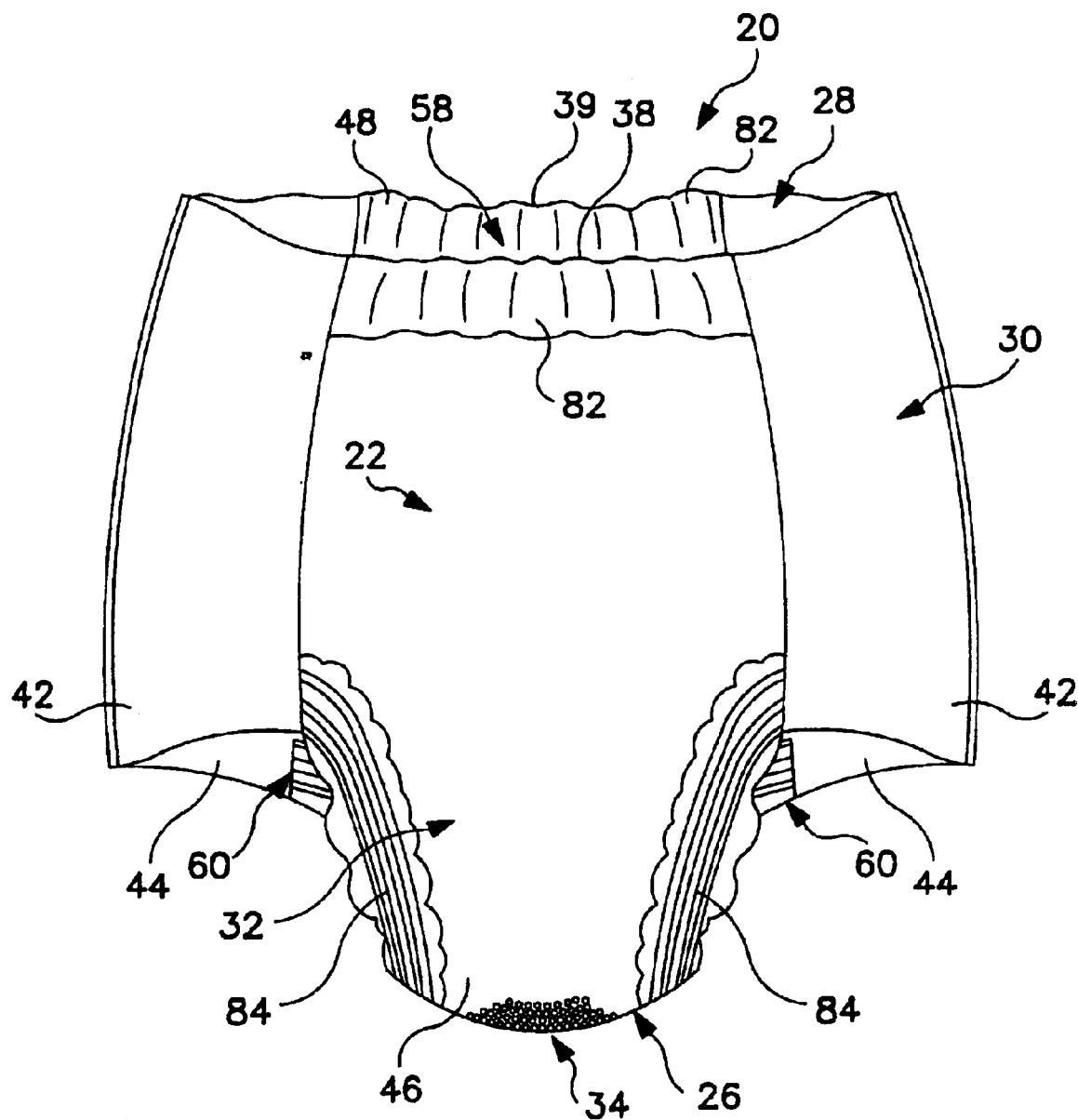
FIG. 1 is a front perspective view of an absorbent swimpant.

Within the context of this specification, each term or phrase below will include the following meaning or meanings.

"Airlaid" refers to a process for making material wherein fibers, such as cellulose-type fibers, are arranged on a wire where they are sprayed with an adhesive. The airlaid material is thus an adhesive-bonded material.

"Coform" refers to a material including a blend of natural fibers and/or synthetic polymer fibers.

"Dispersible" and "dispersibility" refer to the ability of a substance or structure to scatter or separate particles, such as water particles, into various directions. For example, partial dispersibility refers to scattering some, but not all, random particles of a substance into various directions; whereas selective dispersibility refers to scattering certain select particles into various directions.

"Elastic," "elasticized" and "elasticity" mean that property of a material or composite by virtue of which it tends to recover its original size and shape after removal of a force causing a deformation.

"Film" refers to a thermoplastic film made using a film extrusion and (or foaming process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90° are designated "wettable" or hydrophilic, while fibers having contact angles greater than 90° are designated "non-wettable" or hydrophobic.

"Layer" when used in the singular can have the dual meaning of a single element or a plurality of elements.

"Liquid-impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. Liquid, or urine, may spread or be transported parallel to the plane of the liquid impermeable layer or laminate, but this is not considered to be within the meaning of "liquid-impermeable" when used herein.

"Liquid-permeable material," "liquid-semi-permeable material" or "liquid water-permeable material" refers to a material present in one or more layers, or in components, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material, but may be small enough to limit flow of liquid water only above a minimum hydrostatic pressure.

"Meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self-bonding when deposited onto a collecting surface. Meltblown fibers used in the present invention are preferably substantially continuous in length.

"Nonwoven" and "nonwoven web" refer to materials and webs of material which are formed without the aid of a textile weaving or knitting process.

"Polymers" include, but are not limited to, homopolymers, copolymers, such as for example, block, graft, random and alternating copolymers, terpolymers, etc. and blends and modifications thereof Furthermore, unless otherwise specifically limited, the term "polymer" shall include all possible geometrical configurations of the material. These configurations include, but are not limited to isotactic, syndiotactic and atactic symmetries.

"Spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

These terms may be defined with additional language in the remaining portions of the specification.

DETAILED DESCRIPTION OF THE PRESENTLY PREFERRED EMBODIMENTS

The present invention is directed to an absorbent swimwear garment having a built-in draining mechanism for draining excess water, such as pool or lake water, from the garment during and after swimming. The principles of the present invention can be incorporated into disposable, pant-like, absorbent swimwear articles, such as swimpants and swimsuits.

Figure 2:
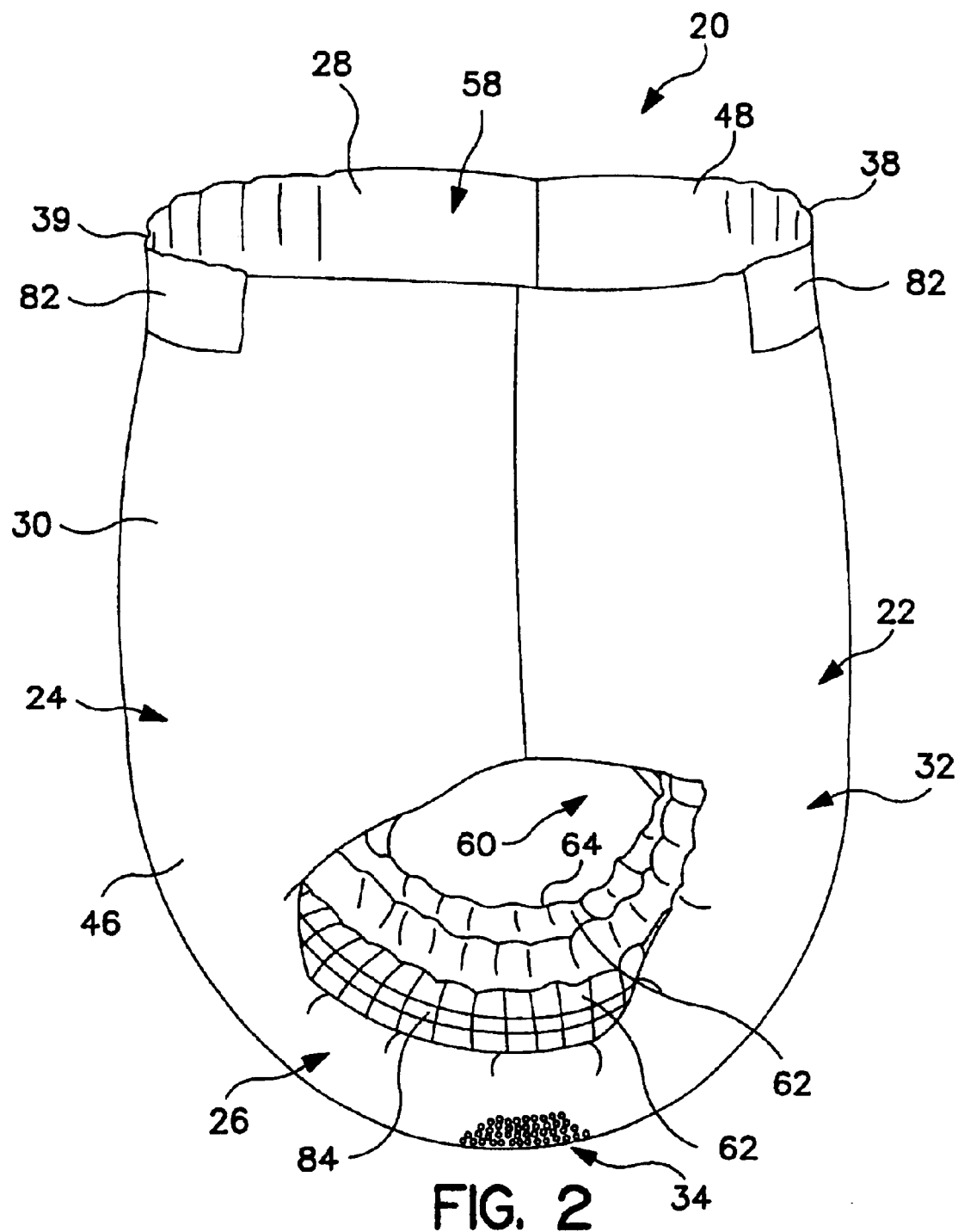
FIG. 2 is a side perspective view of an absorbent swimpant.

Referring to FIGS. 1 and 2, an absorbent swimpant 20 is illustrated. The swimpant 20 includes an absorbent chassis 32. The absorbent chassis 32 defines a front region 22, a back region 24, a crotch region 26 interconnecting the front and back regions, an inner surface 28 which is configured to contact the wearer, and an outer surface 30 opposite the inner surface which is configured to contact a pool or lake environment. The outer surface 30 is at least partially liquid-permeable to allow the release of excess swim water, as explained in greater detail below.

Figure 3:
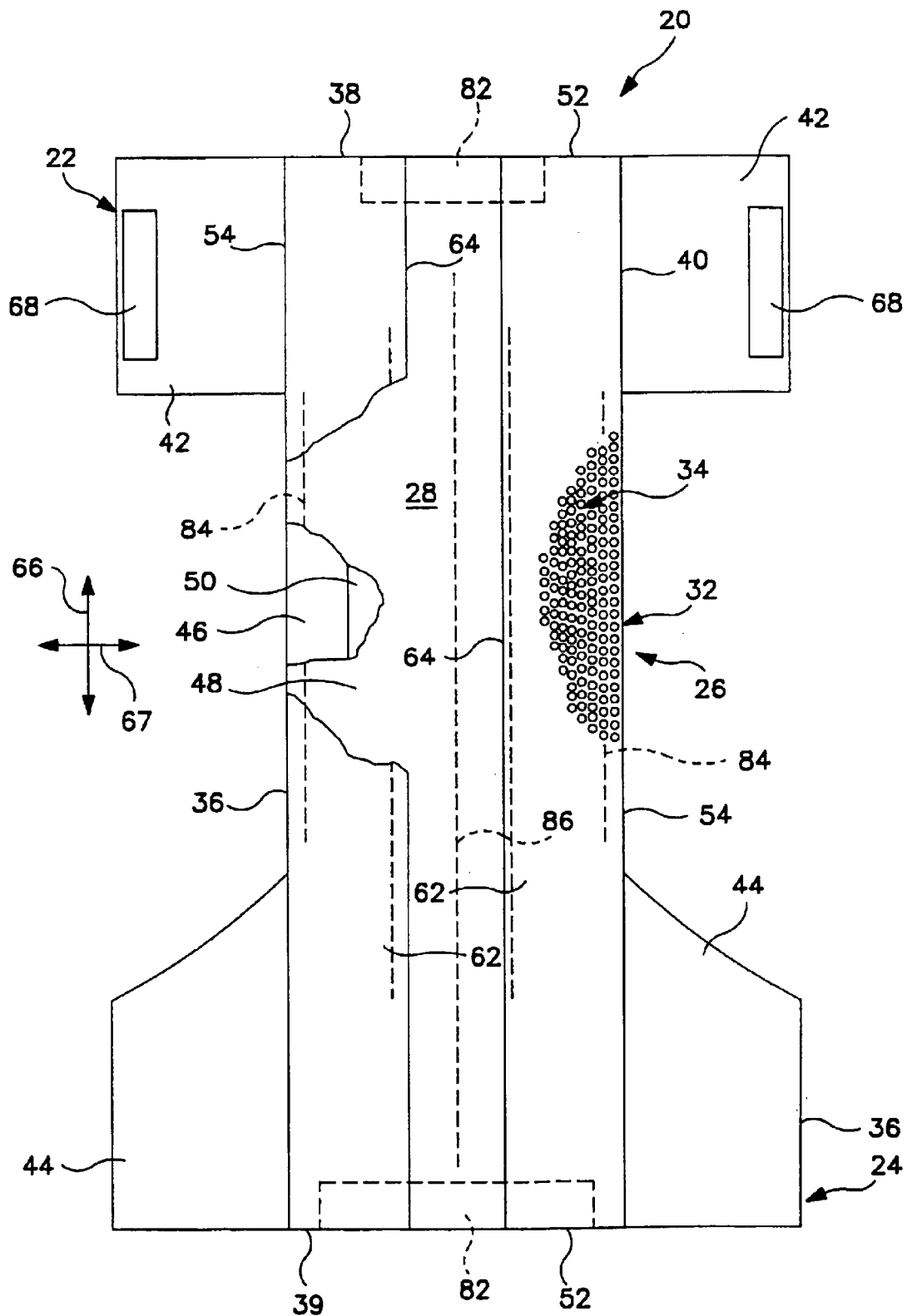
FIG. 3 is a plan view of an absorbent swimpant in a partially disassembled, stretched flat state, and showing the surface of the swimpant that faces the wearer when the swimpant is worn, and with portions cut away to show the underlying features.

Referring to FIG. 3, the swimpant 20 is shown in a partially disassembled, stretched flat state, showing the inner surface 28 which faces the wearer when the garment is worn. As shown, the absorbent chassis 32 also defines a pair of transversely opposed side edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a somewhat rectangular composite structure 40, a pair of transversely opposed front side panels 42, and a pair of transversely opposed back side panels 44. The composite structure 40 and side panels 42 and 44 may be integrally formed, as shown in FIG. 2, or may include two or more separate elements, as shown in FIGS. 1 and 3.

The illustrated composite structure 40 includes an outer cover 46, a body side liner 48 which is connected to the outer cover 46 in a superposed relation, and an absorbent assembly 50 which is located between the outer cover 46 and the body side liner 48. The somewhat rectangular composite structure 40 has opposite linear end edges 52 that form portions of the front and back waist edges 38 and 39, and opposite linear, or curvilinear, side edges 54 that form portions of the side edges 36 of the absorbent chassis 32.

As shown in the swimpants 20 in FIGS. 1 and 2, the front and back regions 22 and 24 together define a three-dimensional pant configuration having a waist opening 58 and a pair of leg openings 60. The waist edges 38 and 39 of the absorbent chassis 32 are configured to encircle the waist of the wearer when worn and provide the waist opening 58 which defines a waist perimeter dimension. Portions of the transversely opposed side edges 36 (FIG. 3) in the crotch region 26 generally define the leg openings 60. The front region 22 includes the portion of the swimpant 20 which, when worn, is positioned on the front of the wearer while the back region 24 includes the portion of the swimpant 20 which, when worn, is positioned on the back of the wearer. The crotch region 26 of the swimpant 20 includes the portion of the swimpant 20 which, when worn, is positioned between the legs of the wearer and covers the lower torso of the wearer.

The absorbent chassis 32 is configured to contain and/or absorb any body exudates discharged from the wearer. For example, the absorbent chassis 32 can include a pair of elasticized containment flaps 62 (shown in FIGS. 2 and 3) which are configured to provide a barrier to the transverse flow of body exudates. More particularly, in terms of swimwear, the containment flaps 62 help prevent the escape of bowel movements from the swimpant 20. Furthermore, the containment flaps 62 provide pre-swim urine leakage protection when the absorbent assembly 50 can no longer acquire the incoming fluid at the rate at which it is being delivered.

The elasticized containment flaps 62 define an unattached edge 64 which assumes an upright, generally perpendicular configuration in at least the crotch region 26 of the swimpant 20 to form a seal against the wearer's body. Suitable constructions and arrangements for the containment flaps 62 are generally well known to those skilled in the art and are described in U.S. Pat. No. 4,704,116 issued Nov. 3, 1987 to Enloe, which is incorporated herein by reference.

Absorbent swimwear is designed for leakage prevention prior to swimming. Thus, when a wearer wears absorbent swimwear into a pool or lake, the swimwear has a tendency to fill up with water in the crotch region 26. Therefore, the swimpant 20 of this invention is equipped with liquid-permeability in the outer surface 30 to alleviate the build-up of excess swim water within the swimpant 20 while still retaining any bowel movement or other solid material within the swimpant 20. More particularly, the outer cover 46 and/or the containment flaps 62 are liquid-permeable, if not over an entire surface area, then over at least part of the surface area of the outer cover 46 and/or the containment flaps 62. This liquid-permeability also results in improved breathability of the swimpant 20 for the prevention of humidity and clamminess within the swimpant 20 prior to swimming.

In one embodiment of the invention, the outer cover 46 is liquid-permeable, at least in the crotch region 26, suitably in the crotch region 26 toward the back region 24. By locating a permeable zone in the bottom of the swimpant 20, i.e., the crotch region 26, the permeable portion can be designed such that it requires a relatively high hydrostatic pressure to induce fluid flow. By requiring high hydrostatic pressure to induce fluid flow, small amounts of fluid having relatively low hydrostatic pressures, i.e., pre-swim urinary insults, can be easily contained within the swimpant 20. As shown in FIGS. 1 and 2, liquid-permeability can be rendered by making a number of holes 34, or slits, in the outer cover 46. These holes 34, or slits, are desirably small enough and/or otherwise designed to block fluid flow to liquids having a hydrostatic pressure, measured using the Hydrostatic Pressure Test Procedure, described below, up to about 1 inch, suitably up to about 2 inches, more suitably up to about 5 inches. Other ways of delivering liquid-permeability, suitably with the same resistance to low hydrostatic pressures, include using liquid-permeable material or inducing permeability through partial or selective dispersibility, or changing the wettability of the pore structure. The effective permeability of the pore structure is lower due to the higher forces required to wet out the pore structure. Once wetted out, the effective permeability of a capillary or pore matrix is lower. The increase in permeability can be effected by partial dispersibility or softening of the barrier material combined with mechanically opening the pores by stresses induced by user movement. Partial or selective dispersibility can be accomplished by using materials that undergo some degree of dissolution when exposed to large quantities of water. The material may be polyvinyl alcohol fibrous webs, films, or laminates. For example, U.S. Pat. No. 5,294,478 issued to Wanek, et al., hereby incorporated by reference, the polyvinyl alcohol molecular weight or treatment is adjusted to give dissolution in large quantities of liquid. Other examples of suitable materials include films of poly lactic acid, hydrophobic tissue, high wet strength tissue and the like.

In another embodiment of the invention, the containment flaps 62 are liquid-permeable. Suitably, the containment flaps 62 have a gradient of permeability, with greater permeability toward the bottom of the swimpant 20. Areas of greater permeability can include either a greater number of pores, slits, or holes 34, or larger sized pores, slits, or holes 34 than areas of lower permeability. More particularly, the containment flaps 62 have greater permeability closer to the crotch region 26 of the chassis 32, and less permeability toward the unattached edge 64. As shown in FIG. 3, liquid-permeability in the containment flaps 62 can be rendered by making a number of holes 34, or slits, in the containment flaps 62. As in the outer cover 46, these holes 34, or slits, are desirably small enough and/or otherwise designed to block fluid flow to liquids having a hydrostatic pressure up to about 0.5 inch, suitably up to about 0.75 inch, more suitably up to about 1.25 inches, as measured by the Flap Simulation Test Procedure, described below. Other ways of delivering liquid-permeability, suitably with the same resistance to low hydrostatic pressures, include using liquid-permeable material or inducing permeability through partial or selective dispersibility.

The absorbent assembly 50 is intended to absorb urine, but does not swell excessively in the presence of swim water, such as pool or lake water. Furthermore, the absorbent assembly 50 is also intended to maintain a low hydrostatic pressure against the liquid-permeable outer cover and/or containment flaps due to urine insults prior to swimming. This can be achieved through the use of surge materials, superabsorbent materials, stabilized airlaid absorbent structures, coform, and the like. The composition of the absorbent assembly 50 is explained in greater detail below. In general, the materials of the absorbent assembly 50 can be configured in various ways to achieve fast intake and to generate void volume in order to prevent excess fluid from reaching the outer cover, the containment flaps, or any other barrier materials. The materials of the absorbent assembly 50 can also be configured to direct incoming fluid parallel to the longitudinal centerline 86 (FIG. 3) of the swimpant 20, and inhibit fluid movement away from the centerline 86 toward the containment flaps, as is known in the art.

For reference, arrows 66 and 67 depicting the orientation of the centerline 86 and the direction perpendicular to the centerline 86, respectively, of the swimpant 20 are illustrated in FIG. 3.

When the swimpant 20 is submerged in water for a length of time, such as when a wearer is swimming or wading in a pool or a lake, the swimpant 20 may fill with water. The water in the swimpant 20 may mix with and dilute any urine in the swimpant 20 that is not held within the absorbent assembly 50. As the wearer exits the water, any water within the swimpant 20 may flow toward the crotch region and, with relatively high hydrostatic pressure, may empty through the liquid-permeable outer cover 46 and/or containment flaps 62. Solid bowel movement material is kept inside the swimpant 20 regardless of any release of swim water, because the body side liner material 48 and other pant components are constructed as in a normal absorbent garment, such as a diaper or training pant, to keep bowel movements contained.

Figure 4:
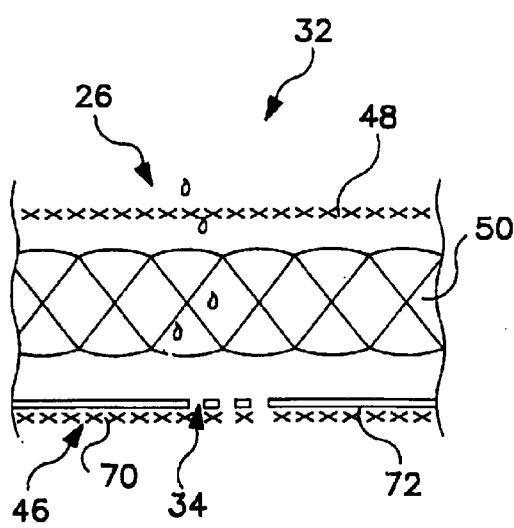
FIG. 4 is a cross-sectional view of the composite chassis of the swimpant before swimming.

FIG. 4 shows a cross-sectional view of the crotch region 26 of the composite chassis 32 of the swimpant 20 before swimming. The body side liner 48 is situated adjacent the wearer's skin when the swimpant 20 is worn. Fluids, i.e., urine, can flow through the body side liner 48 and are then absorbed into the absorbent assembly 50. As mentioned, in one embodiment, the outer cover 46 is liquid-permeable over at least part of the surface area of the outer cover 46, but desirably is permeable only to fluids under a relatively high hydrostatic head, such that substantially all fluids originating within the swimpant 20 stay within the swimpant 20, at least prior to swimming.

Figure 5:
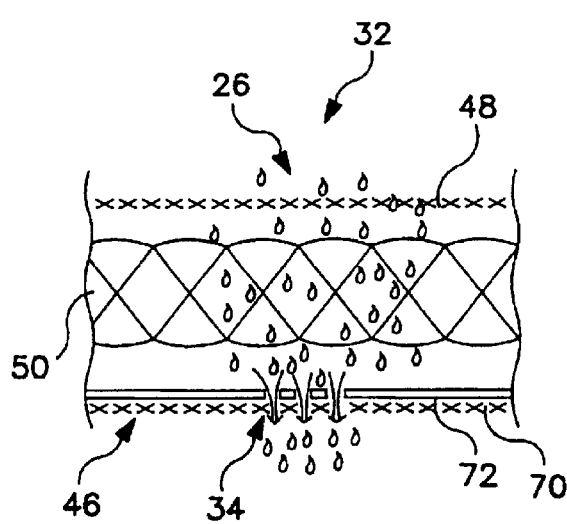
FIG. 5 is a cross-sectional view of the composite chassis of the swimpant during or after swimming.

FIG. 5 shows a cross-sectional view of the crotch region 26 of the composite chassis 32 of the swimpant 20 during or after swimming, when the hydrostatic pressure of the water inside the swimpant 20 may be high enough to permeate through the outer cover 46. The body side liner 48, absorbent assembly 50, and outer cover 46 can be joined together by any suitable means, such as adhesives, as is well known in the art.

The liquid permeable area of the outer cover 46 (FIGS. 1 and 2), i.e., the total area of the outer cover 46 that has at least some pores 34, can cover roughly 5% to about 100% of the entire surface area of the outer cover 46. Suitably, the liquid permeable area covers from about 8% to about 50%, more suitably from about 10% to about 25%. Similarly, the liquid permeable area of the containment flaps 62 (FIG. 3) can cover roughly 5% to about 100% of the entire surface area of the containment flaps 62. Suitably, the liquid permeable area covers from about 10% to about 50%, more suitably from about 10% to about 30%. The individual pores, slits or holes 34 on the outer cover 46 and/or the containment flaps 62 can vary greatly in size, with a length or diameter ranging from about 0.3 mm to about 0.001 mm, for example from about 0.15 mm to about 0.005 mm, or from about 0.075 mm to about 0.01 mm, as long as they satisfy the disclosed hydrostatic pressure requirement. The pores, slits or holes 34 may deform under hydrostatic pressure or user forces such as walking or pressure from sitting to increase size.

The absorbent assembly 50, positioned between the outer cover 46 and the body side liner 48, can be any structure which is generally compressible, conformable, non-irritating to the child's skin, and capable of absorbing and retaining liquids and certain body wastes. The absorbent assembly 50 can be manufactured in a wide variety of sizes and shapes, and from a wide variety of liquid absorbent materials commonly used in the art. For example, the absorbent assembly 50 can suitably include a matrix of hydrophilic fibers, such as a web of cellulosic fluff, and the cellulosic fluff may be mixed with particles of a high-absorbency material commonly known as superabsorbent material. In a particular embodiment, the absorbent assembly 50 includes a matrix of cellulosic fluff, such as wood pulp fluff, and synthetic fibers. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 50 to better contain and absorb body exudates. The concentration of the superabsorbent particles can also vary through the thickness of the absorbent assembly 50. Alternatively, the absorbent assembly 50 can include a laminate of fibrous webs and superabsorbent material or other suitable means of maintaining a superabsorbent material in a localized area. Another type of absorbent material suitable for the absorbent assembly 50 is coform, which is a blend of short fibers and melt-blown fibers. The weight ratio of short fibers to melt-blown fibers may range between 30 (short)/70 (melt-blown) and 90 (short)/10 (melt-blown). Wood pulp fibers are preferred for the short fibers and polypropylene is preferred for the melt-blown fibers. Other short fibers such as short cut polypropylene, polyester, nylon, and the like may be substituted for part of or all of the wood pulp fibers. Superabsorbent materials may be added to the coform to increase capacity.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 50 is generally rectangular in shape, and includes a blend of wood pulp fluff and superabsorbent material. One preferred type of fluff is identified with the trade designation CR 1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 50 in an amount of from about 0 to about 90 weight percent based on total weight of the absorbent assembly 50. The absorbent assembly 50 suitably has a density within the range of about 0.10 to about 0.35 grams per cubic centimeter. The absorbent assembly 50 may or may not be wrapped or encompassed by a suitable tissue wrap that maintains the integrity and/or shape of the absorbent assembly 50.

The outer cover 46 suitably includes a material that is either substantially liquid-permeable or liquid-impermeable, and is desirably at least partially liquid-permeable. More particularly, in the embodiment wherein at least part of the surface area of the outer cover 46 is liquid-permeable, the material used to make the outer cover 46 can either be liquid-permeable material or can be liquid-impermeable material with holes, pores, or slits 34 added to render the material liquid-permeable over at least part of the surface area. In the embodiment wherein at least part of the surface area of the containment flaps 62 is liquid permeable, the material used to make the outer cover 46 can either be liquid-permeable, or liquid-impermeable rendered liquid-permeable through the addition of holes, pores, or slits 34, for added water drainage capability, or can be liquid-impermeable for greater waste retention prior to swimming.

The outer cover material 46 can be elastic, stretchable or nonstretchable. The outer cover 46 can be a single layer of material or a multi-layered laminate structure. For instance, the outer cover 46 can include a liquid permeable outer layer 70 and a liquid permeable inner layer 72 that are suitably joined together by a laminate adhesive (not shown) or by thermal bonding. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. If the outer layer 70 and the inner layer 72 include holes 34 or other types of incisions to provide the permeability, the holes 34 of the layers as assembled are desirably offset from one another to hinder the permeability of fluids under low hydrostatic pressure.

The liquid permeable outer layer 70 can be any suitable material and desirably one that provides a generally cloth-like texture. One example of such a material is a 20 gsm (grams per square meter) spunbond polypropylene nonwoven web. The outer and inner layers 70 and 72 may also be made of those materials of which liquid permeable body side liner 48 is made. While it is not a necessity for the outer layer 70 to be substantially liquid permeable, it is desired that it provides a relatively cloth-like texture to the wearer. Other examples include polyolefin or other thermoplastic nonwoven webs having basis weights of about 1–100 gsm, including spunbond webs, meltblown webs, bonded carded webs, airlaid webs, and combinations of the foregoing, such as spunbond/meltblown webs and spunbond/meltblown/spunbond webs.

The inner layer 72 of the outer cover 46 is desirably manufactured from a thin plastic film, although other flexible liquid impermeable materials may also be used, with holes 34 or other incisions to render the inner layer 72 liquid-permeable. By using a liquid-impermeable film with holes 34 in the crotch region, excess water is directed to the crotch region to exit the swimpant 20. Alternatively, in an embodiment having liquid-permeable containment flaps, the outer cover 46, and particularly the inner layer 72 of the outer cover 46, is liquid-impermeable. An example of a suitable liquid impermeable film for use as a liquid impermeable inner layer 72, or a single layer liquid impermeable outer cover 46, is a 0.02 millimeter polyethylene film commercially available from Huntsman Packaging of Newport News, Va., U.S.A. If the outer cover 46 is a single layer of material, it can be embossed and/or matte finished to provide a more cloth-like appearance.

The liquid impermeable material can permit vapors to escape from the interior of the disposable absorbent article, while still preventing liquids from passing through the outer cover 46. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn. Other similar materials with varying degrees of liquid permeability are spunbond meltblown webs, spunbond/meltblown/spunbond hydrophobic, uniformly formed spunbond, or bi-component webs. A balance of barrier and permeability can be adjusted with fiber size and basis weight.

The containment flaps 62 and/or the outer cover 46, totally or in selected areas, may include materials that undergo some degree of dissolution when exposed to large quantities of water. The material may be poly vinyl alcohol fibrous webs, films, or laminates. One example of a suitable material is described in U.S. Pat. No. 5,294,478 issued to Wanek, et al., wherein the poly vinyl alcohol molecular weight or treatment is adjusted to give dissolution in large quantities of liquid. Other examples of suitable materials include films of poly lactic acid, hydrophobic tissue, high wet strength tissue, and the like.

The liquid-permeable body side liner 48 is illustrated as overlying the outer cover 46 and absorbent assembly 50 (FIG. 3), and may but need not have the same dimensions as the outer cover 46. The body side liner 48 is desirably compliant, soft feeling, and non-irritating to the child's skin. Further, the body side liner 48 can be less hydrophilic than the absorbent assembly 50, to present a relatively dry surface to the wearer.

The body side liner 48 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the body side liner 48. For example, the body side liner 48 can be composed of a meltblown or spunbonded web of polyolefin fibers. The body side liner 48 can also be a bonded-carded web composed of natural and/or synthetic fibers. The body side liner 48 can be composed of a substantially hydrophobic material, and the hydrophobic material can, optionally, be treated with a surfactant or otherwise processed to impart a desired level of wettability and hydrophilicity. For example, the material can be surface treated with about 0.28 weight percent of a surfactant commercially available from the Rohm and Haas Co. under the trade designation Triton X-102. Other suitable surfactants are commercially available from Uniqema in Wilmington, Del., under the trade designation Ahcovel, and from Henkel KGAA Corporation in Dusseldorf, Germany, under the trade designation Glucopon 220. The surfactant can be applied by any conventional means, such as spraying, printing, brush coating or the like. The surfactant can be applied to the entire body side liner 48 or can be selectively applied to particular sections of the body side liner 48, such as the medial section along the longitudinal centerline.

A suitable liquid permeable body side liner 48 is a nonwoven bicomponent web having a basis weight of about 27 gsm. The nonwoven bicomponent can be a spunbond bicomponent web, or a bonded carded bicomponent web. Alternatively, the body side liner 48 can be a 15–30 gsm homofil polypropylene spunbond or bicomponent web. Suitable bicomponent staple fibers include a polyethylene/polypropylene bicomponent fiber available from CHISSO Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 46 and body side liner 48 can include elastomeric materials, it can be desirable in some embodiments for the composite structure to be generally inelastic, where the outer cover 46, the body side liner 48 and the absorbent assembly 50 include materials that are generally not elastomeric.

The containment flaps 62 may be made of those materials of which the outer cover 46 and/or the body side liner 48 is made.

As noted previously, the illustrated training pant 20 can have front and back side panels 42 and 44 disposed on each side of the absorbent chassis 32 (FIGS. 1 and 3). These transversely opposed front side panels 42 and transversely opposed back side panels 44 can be permanently bonded to the composite structure 40 of the absorbent chassis 32 and can be permanently bonded to one another along corresponding sides. Alternatively, the front and back side panels 42, 44 can be releasably attached to one another by a fastening system 68. The side panels 42 and 44 may be attached to the composite structure 40 and/or to one another using attachment means known to those skilled in the art such as adhesive, thermal or ultrasonic bonding. The side panels 42 and 44 can also be formed as a portion of a component of the composite structure 40, such as the outer cover 46 or the body side liner 48.

Suitable elastic materials, as well as one described process of incorporating elastic side panels into an absorbent garment, are described in the following U.S. Pat. Nos.: 4,940,464 issued Jul. 10, 1990 to Van Gompel et al.; 5,224,405 issued Jul. 6, 1993 to Pohjola; 5,104,116 issued Apr. 14, 1992 to Pohjola; and 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 46 or body side liner 48, or stretchable but inelastic materials.

To further enhance containment and/or absorption of body exudates, the swimpant 20 can include waist elastic members 82 and/or leg elastic members 84, as are known to those skilled in the art (FIGS. 1–3). The waist elastic members 82 can be operatively joined to the outer cover 46 and/or to the body side liner 48, and can extend over part or all of the waist edges 38, 39. The leg elastic members 84 are desirably operatively joined to the outer cover 46 and/or to the body side liner 48 longitudinally along the opposite side edges 36 and positioned in the crotch region 26 of the swimpant 20.

The waist elastic members 82 and the leg elastic members 84 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the waist elastic members 82 and/or the leg elastic members 84 include a plurality of dry-spun coalesced multifilament spandex elastomeric threads sold under the trade name LYCRA® and available from E. I. du Pont de Nemours and Company, Wilmington, Del., U.S.A. In another particular embodiment, for example, the waist elastic members 82 and/or the leg elastic members 84 include Findley HX 2695-01 adhesive laminated to two facings of 0.6 osy bicomponent polypropylene/polyethylene spunbond. Alternatively, six strands of 310 decitex LYCRA® may be also laminated at 250% elongation between the spunbond facings in addition to the Findley adhesive.

As described herein, the various components of the swimpant 20 can be integrally assembled together employing various types of suitable attachment means, such as adhesive, sonic and thermal bonds or combinations thereof. The resulting product is an absorbent swimwear garment 20 that provides uncompromised urine and bowel movement containment before swimming, but allows draining of excess water from the garment 20 after swimming without substantially altering bowel movement containment.

EXAMPLES

Hydrostatic Pressure Test Procedure

In this test, water pressure is measured to determine how much water pressure is required to induce leakage in three separate areas of a test material. The water pressure is reported in millibars at the first sign of leakage in three separate areas of the test specimen. The pressure in millibars can be converted to hydrostatic head height in inches of water by multiplying millibars by 0.402. Pressure measured in terms of inches refers to pressure exerted by a number of inches of water. Hydrostatic pressure is pressure exerted by water at rest.

Apparatus used to carry out the procedure includes a hydrostatic head tester, such as TEXTEST FX-3000 available from ATI Advanced Testing Instruments Corp. of Spartenburg, S.C., a 25.7 cm$^2$ test head such as part number FX3000-26 also available from ATI Advanced Testing Instruments Corp., purified water such as distilled, deionized, or purified by reverse osmosis, a stopwatch accurate to 0.1 second, a one-inch circular level, and a cutting device, such as scissors, a paper cutter, or a die-cutter.

Prior to carrying out this procedure, any calibration routines recommended by manufacturers of the apparatus being used should be performed. Using the cutting device, the specimen is cut to the appropriate size. Each specimen has a minimum size that is sufficient to allow material to extend beyond the outer diameter of the test head. For example, the 25.7 cm² test head requires a 6-inch by 6-inch, or 6-inch diameter specimen. Specimens should be free of unusual holes, tears, folds, wrinkles, or other distortions.

First, make sure the hydrostatic head tester is level. Close the drain faucet at the front of the instrument and pull the upper test head clamp to the left side of the instrument. Pour approximately 0.5 liter of purified water into the test head until the head is filled to the rim. Push the upper test head clamp back onto the dovetail and make sure the plug is inserted into the socket at the left side of the instrument. Turn the instrument on and allow the sensor to stabilize for 15 minutes. Make sure the Pressure Gradient thumbwheel switch is set to 60 mbar/min. Make sure the drain faucet is closed. The water temperature should be maintained at about 75° Fahrenheit±10° Fahrenheit. Use the Light Intensity adjustment to set the test head illumination for best visibility of water droplets passing through the specimen.

Once the set-up is completes slide the specimen onto the surface of the water in the test head, from the front side of the tester. Make sure there are no air bubbles under the specimen and that the specimen extends beyond the outer diameter of the test head on all sides. If the upper test head clamp was removed for loading the specimen, push the clamp back onto the dovetail. Pull down the lever to clamp the specimen to the test head and push the lever until it comes to a stop. Press the Reset button to reset the pressure sensor to ZERO. Press the Start/Pause button to start the test. Observe the specimen surface and watch for water passing through the specimen. When water droplets form in three separate areas of the specimen, the test is complete. Any drops that form within approximately 0.13 inch (3.25 mm) of the edge of the clamp should be ignored. If numerous drops or a leak forms at the edge of the clamp, repeat the test with another specimen. Once the test is complete, read the water pressure from the display and record. Press the Reset button to release the pressure from the specimen for removal. Repeat procedure for desired number of specimen repeats.

Flap Simulation Test Procedure

This test was developed in the laboratory to simulate water pressure building up against a barrier flap in the vertical position. This test measures the water pressure height at which the test material releases liquid and the resulting water height after draining is complete. The test material can be the material used to make flaps rather than using an actual pre-fabricated flap. Unlike the pre-fabricated flap, the test material does not have elastics and is not limited to the size or shape of pre-fabricated flaps.

Apparatus used to carry out the procedure includes a four-sided sample holder wherein an open side is covered with the test material, the other three sides and bottom are a rigid, liquid-impermeable, preferably clear material, and liquid can be input through a top opening in the sample holder. Appropriate dimensions for the sample holder can be 75 mm wide, 40 mm tall, and 30 mm long, such that the open side can be 75 mm×40 mm. One end, i.e., a 30 mm×40 mm wall, suitably is marked with fluid height markings at 5 mm intervals. In addition to the sample holder, other apparatus used includes adhesive transfer tape, such as 3M Brand 922XL, and a liquid delivery apparatus, such as a Masterflex DIGI-STALTIC® peristaltic pump Model 7526-00 with a Masterflex Model 7017-21 pump head, available from Cole-Parmer Instrument Company Corporation of Chicago, Ill.

The specimen is cut to fit over the open side of the sample holder. The specimen should be cut slightly larger than the open area such that the specimen overlaps the sides and bottom of the holder. Next, release paper is removed from pieces of adhesive transfer tape, and the pieces of adhesive transfer tape are applied to the sides of the sample holder that support the test specimen. The test specimen is placed over the adhesive on the holder and is firmly pressed into place using thumb pressure to ensure a proper seal between the specimen and the holder. Optionally, the sample holder can be placed on a piece of blotter paper.

Once the set-up is complete, a liquid delivery apparatus is used to add water to the sample holder via the top opening at a rate of approximately 95 ml/minute. Tap water colored with a small amount of FD&C Blue #1 dye is a suitable choice of liquid to be used in this test. The outer surface of the test specimen is then watched. When at least one droplet of water appears on the outer surface of the specimen, the liquid addition to the sample holder must be stopped and the water height recorded from the markings on the side of the holder. The droplets of water typically emerge at or close to the bottom of the sample holder. The specimen is continued to be monitored as the water drains from the sample holder. When the water stops draining, the final water height in the holder is recorded from the markings on the side of the holder.

TABLE 1

Test Results

| Material | Hydrohead (inches) | Flap Simulation Release Height (inches) | Flap Simulation Final Height (inches) |
|---|---|---|---|
| 0.8 osy, 1 dpf (denier per filament), spunbond | 5.66 | >1.38 | no draining |
| 1.0 osy, 1 dpf, spunbond | 7.15 | >1.38 | no draining |
| 1.2 osy, 1 dpf, spunbond | 8.23 | >1.38 | no draining |
| untreated necked-creped spunbond | 2.45 | 1.31 | 0.46 |
| treated necked-creped spunbond* | 1.25 | 0.77 | 0.20 |
| 0.4 osy, 2 dpf through-air-bonded, 50/50 polyethylene/polypropylene side-by-side bicomponent spunbond fibers | 1.24 | did not test | |
| 0.7 osy, 2 dpf through-air-bonded, 50/50 polyethylene/polypropylene side-by-side bicomponent spunbond fibers | 3.33 | did not test | |
| 1.2 osy, 2 dpf through-air-bonded, 50/50 polyethylene/polypropylene side-by-side bicomponent spunbond fibers | 4.74 | did not test | |
| 0.6 osy, 3 dpf bi-component web | 0.98 | 0.68 | 0.16 |

*Surfactant-treated for wettability with Ahcovel

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent swimwear garment comprising:
a chassis defining a waist opening and first and second leg openings with a crotch area between the first and second leg openings, the chassis including a liquid-permeable body side liner, a selectively liquid-permeable outer cover having a crotch area that is more liquid-permeable than the rest of the outer cover, wherein a liquid that permeates the outer cover can be expelled through the outer cover into an open environment outside of the garment, and an absorbent assembly between the body side liner and the outer cover wherein the absorbent assembly is selected from a web comprising cellulosic fluff and a web comprising superabsorbent material.

2. The absorbent garment of claim 1, wherein the outer cover is liquid-permeable only to liquids having a hydrostatic pressure greater than about 1 inch.

3. The absorbent garment of claim 1, wherein the outer cover is liquid-permeable only to liquids having a hydrostatic pressure greater than about 2 inches.

4. The absorbent garment of claim 1, wherein the outer cover is liquid-permeable only to liquids having a hydrostatic pressure greater than about 5 inches.

5. The absorbent garment of claim 1, further comprising a plurality of apertures in the crotch area of the outer cover.

6. The absorbent garment of claim 1, wherein the absorbent assembly directs incoming aqueous fluids away from the crotch area.

7. An absorbent swimwear garment comprising:
a chassis defining a waist opening and first and second leg openings with a crotch area between the first and second leg openings, the chassis including a liquid-permeable body side liner, a partially liquid-permeable outer cover having a crotch area that is more liquid-permeable than the rest of the outer cover, wherein a liquid that permeates the outer cover can be expelled through the outer cover into an open environment outside of the garment, and an absorbent assembly between the body side liner and the outer cover wherein the absorbent assembly is selected from a web comprising cellulosic fluff and a web comprising superabsorbent material.

8. The absorbent garment of claim 7, wherein the outer cover is liquid-permeable only to liquids having a hydrostatic pressure greater than about 1 inch.

9. The absorbent garment of claim 7, wherein the outer cover is liquid-permeable only to liquids having a hydrostatic pressure greater than about 2 inches.

10. The absorbent garment of claim 7, wherein the outer cover is liquid-permeable only to liquids having a hydrostatic pressure greater than about 5 inches.

11. The absorbent garment of claim 7, further comprising a plurality of apertures in the crotch area of the outer cover.

12. The absorbent garment of claim 7, wherein the absorbent assembly directs incoming aqueous fluids away from the crotch area.

13. An absorbent swimwear garment comprising:
a chassis defining a waist opening and first and second leg openings with a crotch area between the first and second leg openings, the chassis including a body side liner, an outer cover wherein a liquid that permeates the outer cover can be expelled through the outer cover into an open environment outside of the garment, an absorbent assembly between the body side liner and the outer cover wherein the absorbent assembly is selected from a web comprising cellulosic fluff and a web comprising superabsorbent material, and a pair of liquid-permeable containment flaps adjacent the first and second leg openings in the crotch area;

the crotch area of the garment being more liquid-permeable than the rest of the garment, wherein the crotch area of the containment flaps are more liquid-permeable than the rest of the containment flaps.

14. The absorbent garment of claim 13, wherein the crotch area of the outer cover is liquid-permeable only to liquids having a hydrostatic pressure greater than about 1 inch.

15. The absorbent garment of claim 13, wherein the crotch area of the outer cover is liquid-permeable only to liquids having a hydrostatic pressure greater than about 2 inches.

16. The absorbent garment of claim 13, wherein the crotch area of the outer cover is liquid-permeable only to liquids having a hydrostatic pressure greater than about 5 inches.

17. The absorbent garment of claim 13, wherein 5% to 100% of surface area of the outer cover is liquid-permeable.

18. The absorbent garment of claim 13, wherein 8% to 50% of surface area of the outer cover is liquid-permeable.

19. The absorbent garment of claim 13, wherein 10% to 25% of surface area of the outer cover is liquid-permeable.

20. The absorbent garment of claim 13, further comprising a plurality of apertures in the crotch area of the outer cover.

21. The absorbent garment of claim 13, wherein the containment flaps are liquid-permeable only to liquids having a hydrostatic pressure greater than about 0.5 inch.

22. The absorbent garment of claim 13, wherein the containment flaps are liquid-permeable only to liquids having a hydrostatic pressure greater than about 0.75 inch.

23. The absorbent garment of claim 13, wherein the containment flaps are liquid-permeable only to liquids having a hydrostatic pressure greater than about 1.25 inches.

24. The absorbent garment of claim 13, wherein 5% to 100% of surface area of the containment flaps is liquid-permeable.

25. The absorbent garment of claim 13, wherein 10% to 50% of surface area of the containment flaps is liquid-permeable.

26. The absorbent garment of claim 13, wherein 10% to 30% of surface area of the containment flaps is liquid-permeable.

27. The absorbent garment of claim 13, wherein the containment flaps comprise a gradient of permeability, with a first longitudinal edge of each flap having greater permeability than a second longitudinal edge of each flap.

28. The absorbent garment of claim 27, wherein the first longitudinal edge of each flap is attached to the chassis.

29. The absorbent garment of claim 13, further comprising a plurality of apertures in the containment flaps.

30. The absorbent garment of claim 13, wherein the absorbent assembly directs incoming aqueous fluids away from the containment flaps.

* * * * *